United States Patent [19]

Knoepfler

[11] Patent Number: 5,312,331
[45] Date of Patent: May 17, 1994

[54] METHOD AND APPARATUS FOR TALC PLEURODESIS

[76] Inventor: Dennis J. Knoepfler, 1383 Whitaker La., Amelia, Ohio 45102

[21] Appl. No.: 47,320

[22] Filed: Apr. 15, 1993

[51] Int. Cl.$^5$ .......................................... A61M 31/00
[52] U.S. Cl. ........................................ 604/49; 604/58; 239/590.5
[58] Field of Search ...................... 128/203.15, 203.21, 128/203.24, 200.23; 604/36-39, 54, 55, 58, 49, 289; 222/631-633, 571; 239/590, 590.5, 553, 553.5, 601

[56] References Cited

U.S. PATENT DOCUMENTS

| | | | |
|---|---|---|---|
| 1,732,566 | 10/1929 | McKendrick | 604/58 |
| 2,122,234 | 6/1938 | McAuliffe | 128/203.15 |
| 2,570,774 | 10/1951 | Davis | 128/203.15 |
| 2,754,097 | 7/1956 | Hjulian | 239/590.5 |

FOREIGN PATENT DOCUMENTS

| | | | |
|---|---|---|---|
| 619625 | 10/1935 | Fed. Rep. of Germany | 604/58 |
| 2608930 | 7/1988 | France | 604/36 |

OTHER PUBLICATIONS

Treatment of Malignant Pleural Effusion: A Method Using Tube Throracostomy and Talc, Adler et al. Annals of Thoracic Surgery, vol. 22, No. 1, Jul, 1976.
Iodized Talc Pleurodesis for Treatment of Pleural Effusions, Webb et al, Journal of Thoracic and Cardiovascular Surgery vol. 103, No. 5, May, 1992.
W. R. Webb et al: Iodized Talc Pleurodesis For The Treatment Of Pleural Effusions; J. Thorac Cardiovasc Surg. (May 1992), vol. 103, No. 6, pp. 881-886.
P. Lange et al: Lung Function 22-35 Years After Treatment Of Idiopathic . . . , Thorax (Jul 1988), vol. 43, pp. 559-561.
B. L. Fingar: Sclerosing Agents Used To Control Malignant Pleural Effusions; Hosp. Pharm. (Jul. 1992), vol. 27, pp. 622-628.
H. Hamed et al: Comparison Of Intracavitary Bleomycin and Talc For Control . . . ; Br. J. Surg., vol. 76, No. 12, Dec. 1989, pp. 1266-1267.
Tunon-da-Lara et al: Spontaneous Pneumothorax Associated With Pneumocystis . . . ; Chest., vol. 101, No. 4, Apr. 1992, pp. 1177-1178.
S. K. Ohri et al: Early and Late Outcome After Diagnostic Thoracoscopy . . . ; Ann. Thorac. Surg., Jun. 1992, vol. 53, No. 6, pp. 1038-1041.
M. Almind et al: Spontaneous Pneumothorax: Comparison of Simple Drainage . . . ; Thorax, vol. 44, No. 8, Aug. 1989, pp. 627-630.
R. H. Adler et al: Treatment of Malignant Pleuroal Effusion: A Method Using . . . ; The Annals of Thoracic Surgery, vol. 22, No. 1, Jul. 1976, pp. 8-15.
W. R. Webb et al: Iodized Talc Pleurodesis For The Treatment of Pleural . . . ; The J. of Thoracic & Cardiov. Surgery, vol. 103, No. 5, May 1992, pp. 881-886.
T. M. Daniel: Thoracoscopy and Talc Poudrage for Pneumothoraces . . . ; Ann Thorac Surg. vol. 50, 1990, pp. 186-187.

Primary Examiner—Jerome L. Kruter
Attorney, Agent, or Firm—Wood, Herron & Evans

[57] ABSTRACT

An apparatus for conducting a talc pleurodesis includes a thoracic tube which includes a talc chamber. At one end of said tube is a rubber bulb. In the opposite end of the tube is a tip that includes a constriction or valve. Talc is placed into the talc chamber and the tip is inserted into the chest cavity between the lung and the chest cavity. The bulb is then pressed forcing air through the tube and forcing talc into the chest cavity. The constriction prevents the talc from free flowing through the end of the tube. However, the constriction is such that under pressurized air, the talc can flow from the tip. This permits pleurodesis to be conducted with dry talc very easily and evenly under direct vision with the aid of a thorascope.

8 Claims, 1 Drawing Sheet

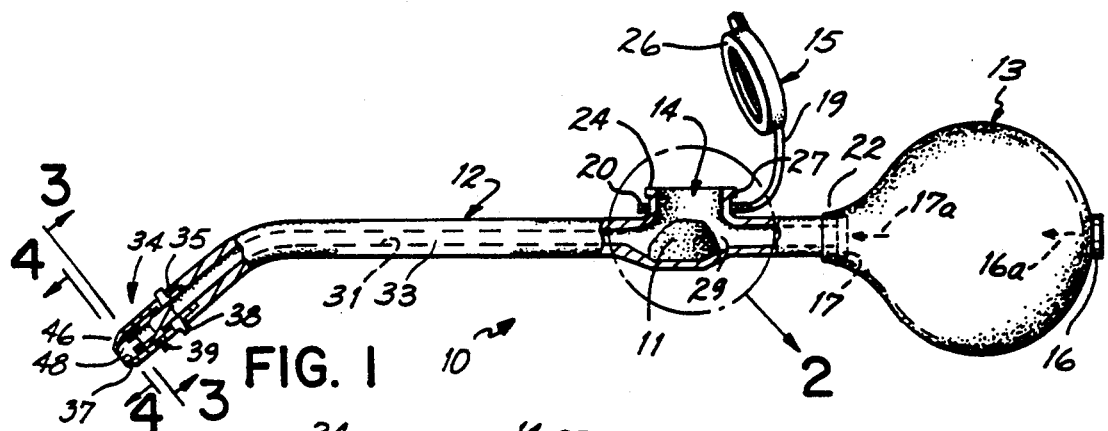
FIG. 1
FIG. 2
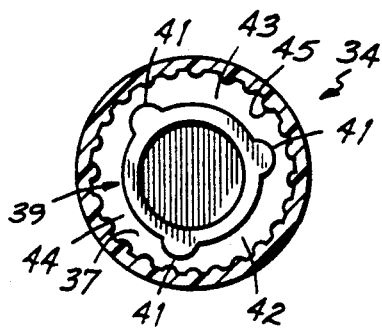
FIG. 3
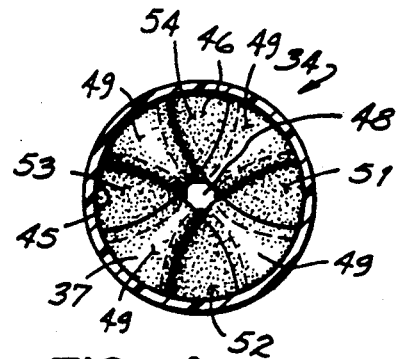
FIG. 4

METHOD AND APPARATUS FOR TALC PLEURODESIS

BACKGROUND OF THE INVENTION

Pleurodesis is an operative procedure designed to prevent a lung from collapsing or recollapsing after inflation. Particularly patients who suffer from spontaneous pneumothorax or pleura effusions, for example, those patients with lung cancer and/or acquired immune deficiency will frequently suffer collapsed lungs.

Treatment includes draining the pleural space and reinflating the lung. The outer lung wall or visceral pleura is then bonded to the parietal pleura. In pleurodesis, this is done by scarring the visceral and parietal pleura so that upon healing, they bond to each other.

This is generally accomplished with a thoracostomy tube procedure. In this procedure, a scarring agent, such as tetracycline or a saline slurry of talc is administered into the pleural space through the thoracostomy tube. Movement of the patient causes the scarring agent to flow around the chest cavity. Upon healing, the lung is bonded to the chest cavity preventing a recollapse of the lung. The talc powder can also be administered with an insufflator or syringe.

Utilizing an aqueous slurry or an aqueous solution requires that the material be spread evenly around the area that requires repeated movement of the patient. This requirement makes the result relatively questionable because it is difficult to ensure even coating of the slurry over the affected area.

Further, when talc is applied, it must be combined with saline and agitated to form a uniform slurry. This is time consuming. The use of an insufflator to administer powdered talc is advantageous but the talc can simply flow out the end of the insufflator. This makes an insufflator very difficult to use.

SUMMARY OF THE INVENTION

Accordingly, it is an object of the present invention to provide a simple, convenient and easy method to perform pleurodesis.

Further, it is an object of the present invention to provide an apparatus designed to apply powdered talc over a lung surface during pleurodesis.

According to the present invention, there is a thorascopic powder applicator which includes an elongated tube with a bulb at one end and a tip at the opposite end. Intermediate the two ends is a resealable powder chamber which has an opening adapted to receive talc. Since talc is so fine, an open-ended tube would simply permit the talc to flow out of the tube. Accordingly, the opposite end of the tube includes a restriction or pressure valve which narrows the tube opening and in turn keeps the talc from flowing out of the tube until the bulb is constricted forcing air and talc through and out of the tube. There is also a one-way valve on each side of the bulb which allows air to enter and exit the bulb in one direction and also allows repeated immediate repumping of the bulb to evacuate the chamber entirely.

This can be used in a pleurodesis by simply inserting this second end of the tube into the pleural space, placing talc within the tube, sealing the talc chamber and squeezing the bulb. This will spread a uniform cloud of powder over the affected area ensuring uniform application. This is ensured because the thoracoscope which is already in place allows you to directly visualize the distribution of the talc powder. Further, this does not have to be premixed to form a slurry and, of course, does not require subsequent movement of the patient. Further, additional talc can be added to the chamber so that an appropriate amount of talc can be administered.

The present invention will be further appreciated in light of the following detailed description and drawings in which:

BRIEF DESCRIPTION OF THE DRAWINGS

FIG. 1 is a side elevational view partially in cross-section of the present invention;

FIG. 2 is an enlarged cross-sectional view of the circled portion of FIG. 1;

FIG. 3 is a cross-sectional view taken at lines 3—3 of FIG. 1; and

FIG. 4 is a cross-sectional view taken at lines 4—4 of FIG. 1.

DETAILED DESCRIPTION

As shown in FIG. 1, the present invention is a powder dispenser 10 primarily adapted to dispense talc 11 in a thorascopic pleurodesis procedure. As such, the dispenser 10 includes rigid elongated plastic tube 12, a bulb 13, and a powder chamber 14.

Bulb 13 includes two one-way valves, a one-way inlet valve 16 at the extreme upstream end of bulb 13, and a one-way outlet valve 17 which is immediately adjacent end 22 of tube 12. These valves 16 and 17 permit air flow only in the direction shown by arrows 16a and 17a.

The powder chamber 14 is accessible through cap 15. Inner annular rim 26 of cap 15 is adapted to snap fit over a flange 27 of chamber 14. This holds the cap 15 in position on the upper edges of wall 24 sealing chamber 14. Cap 15 also includes a tab 19 connected to ring 20 which is attached to the wall of chamber 14 and is held in place by flange 27.

As shown in FIG. 2, the inner area 29 in the powder chamber 14 includes a large central area where talc 11 is placed. This generally tapers, along wall 31 to a diameter at outlet 32 of about 0.3 inches. This diameter continues throughout the middle section 33 of the tube 12 and this diameter continues until the distal end 23. The tube 12 includes a bend 23 (approximately 40°) between the distal end 23 and middle section 33. As will be described below, this permits the talc to be more easily dispensed throughout the entire pleural space.

As shown in FIG. 1, the distal end 23 of tube 12 includes a tip 34. Tip 34 includes a narrow tubular portion 35 which is adhered to an enlarged portion of end 23. This tubular portion 35 is separated from an outlet chamber 37 by a small annular flange 38.

As shown in FIGS. 1 and 3, the outlet chamber 37 includes a cylindrical plug 39 which is smaller than the inside diameter of the outlet chamber 37. Plug 39 includes three spaced axial ridges 41 along its exterior surface. This divides the chamber into three curved passages 42, 43, and 44.

As shown in FIG. 3, the interior wall 45 of the chamber 37 is fluted which provides a plurality of axial passageways through the chamber. Chamber 37 has a rounded end 46 which includes an exit opening 48. This end 46 is formed by simply crimping the exterior walls of chamber 37 which forms four ridges 49 which engage the plug 39 and provides four small passageways 51-54 from the curved passageways 42-44 to the opening 48. The general size of the openings is sufficient so that the talc when it is in the tube will not, by force of gravity, flow through the opening. A tip suitable for this purpose can be purchased from Halkey Roberts Company.

To inject the talc into the chest cavity, a patient is placed on their side, preferably in a bolster that helps spread the ribs. Fluid in the chest cavity is drained by inserting a tube generally in the eighth or ninth intercostal space of the posterior auxiliary line. A hemostat is used to create a path through the intercostal space and to puncture the pleura so that a number 32 argyle plastic catheter within a introcar can be inserted easily without pressure. The fluid is drained from the chest into a plastic water seal suction unit (pleurovac) as rapidly as the patient can tolerate. A portable chest roentgenogram is taken to confirm complete fluid evacuation in the lung expansion. The tube is then removed and the tube 12 of device 10 is inserted through the trocar. A thorascope is also placed through another 10 MM trocar that is inserted into the chest cavity. Then under direct vision with the thorascope, the talc powder can be evenly dispensed over the entire pleural cavity.

Generally, 1 to about 10 grams of talc will be employed depending on the size and condition of the patient. The chamber 14 will adequately hold about 10 grams of talc. But, it should be filled no more than half full to allow good air flow through the chamber 29.

The talc is placed into the chamber 14 and the chamber 14 sealed with cap 15. Generally, the talc will naturally flow by gravity down through the tube and stop at plug 39. The bulb 13 is rapidly squeezed forcing air from the bulb 13 in the direction of arrow 17a forcing the talc through the tube into chamber 37 where it will flow around the plug 39 and out opening 48. This is then repeated until the entire desired amount of talc is blown into the pleural cavity. Because tube 12 is bent, the tip can be easily directed to any desired location by simply rotating the tube 12. This will coat the parietal pleura and the visceral pleura causing scarring. When this heals, it will keep the parietal pleura attached to the visceral pleura preventing the lung from recollapsing.

This method, of course, avoids many of the problems encountered with talc pleurodesis. The talc is applied where it is desired immediately. There is no need to move the patient around and cause discomfort to the patient. Further, since this is blown in with a blast of air, more even distribution of the talc should be attained. Further, this does not require any mixing of the talc with saline nor does it add any additional liquid into the chest cavity which would need to be drained. This provides less pressure against the lung again maintaining it in an inflated condition.

Further, this device is very inexpensive and no more complex than a syringe which is typically used to inject the saline slurry of talc into the chest cavity. Accordingly, it is very inexpensive and, of course, simple to use.

In particular, the procedure can be repeated to administer the desired amount of talc without removing the apparatus from the patient. This significantly simplifies this procedure.

This has been a description of the present invention along with the preferred method of practicing the present invention.

However, the invention itself should be defined only by the appended claims wherein we claim:

1. An apparatus for applying powdered talc in a chest cavity comprising:
   an elongated tube having a first end and a second end opposite said first end and a talc chamber means intermediate said first and second ends, said talc chamber means containing powdered talc for performing a pleurodesis procedure on a patient;
   means at said second end to force air from said second end to said first end; and,
   a constriction formed in an outlet chamber means at said first end which prevents said powdered talc from flowing out of said first end except when pressurized air is forced through said tube, said constriction being formed by a plug centrally disposed in said outlet chamber means said plug including spaced axial ridges on an outer surface thereof which define a plurality of restricted pathways between said outer surface of said plug and an inner wall of said outlet chamber means.

2. The apparatus claimed in claim 1 wherein said talc chamber means is immediately downstream of said means to force air through said tube.

3. The apparatus claimed in claim 2 wherein said talc chamber means includes an access opening and means to seal said access opening.

4. The apparatus claimed in claim 1 wherein said plug is a cylindrical member and wherein said outlet chamber means includes axial flutes disposed on said inner wall thereof.

5. A method of conducting a pleurodesis comprising:
   forming an incision to access an area between a patient's chest cavity and lung and draining fluid within said area;
   inserting a rigid tube into said incision wherein a tip of said tube is between a surface of said lung and said chest cavity to coat the pleuro;
   placing powdered talc into said tube, permitting said talc to flow to said tip by gravity force and preventing the flow of said talc from exiting said tube through said tip by providing an obstruction of an outlet opening of said tip;
   forcing air through said tube to force talc out of said outlet opening of said tip and into said area by compressing a bulb attached to a second end of said tube to force air in said bulb through said tube.

6. The method of claim 5 further comprising the step of:
   adding additional talc into said tube and forcing air through said tube again to force said talc into said cavity wherein at least about 1 to about 10 grams of talc is injected into said area.

7. The method of claim 5 wherein said obstruction is a plug disposed within said tip and having spaced axial ridges on an outer surface thereof and said step of forcing air through said tube further comprises forcing said talc between said spaced axial ridges.

8. The method of claim 7 wherein said tip includes an inner surface having axial flutes disposed thereon and the step of forcing air through said tube further comprises:
   forcing talc between said axial flutes as well as between said flutes and said ridges and out said outlet opening of said tip.

* * * * *